US006540962B1

(12) United States Patent
Okubo et al.

(10) Patent No.: US 6,540,962 B1
(45) Date of Patent: Apr. 1, 2003

(54) TESTING INSTRUMENT FOR ANALYZING LIQUID SAMPLE

(75) Inventors: Akio Okubo, Kyoto (JP); Atsuko Katayama, Kyoto (JP); Yoshiyuki Tanaka, Kyoto (JP); Yoshihiko Higuchi, Kyoto (JP); Masufumi Koike, Kyoto (JP)

(73) Assignee: Kyoto Daiichi Kagaku Co., Ltd., Kyoto-fu (JP)

( * ) Notice: Subject to any disclaimer, the term of this patent is extended or adjusted under 35 U.S.C. 154(b) by 0 days.

(21) Appl. No.: 09/380,838

(22) PCT Filed: Mar. 11, 1998

(86) PCT No.: PCT/JP98/01010

§ 371 (c)(1), (2), (4) Date: Dec. 9, 1999

(87) PCT Pub. No.: WO98/40735

PCT Pub. Date: Sep. 17, 1998

(30) Foreign Application Priority Data

| | | |
|---|---|---|
| Mar. 3, 1997 | (JP) | 9-078852 |
| Oct. 3, 1997 | (JP) | 9-288005 |
| Oct. 23, 1997 | (JP) | 9-309872 |
| Oct. 23, 1997 | (JP) | 9-309873 |
| Oct. 23, 1997 | (JP) | 9-309874 |
| Oct. 23, 1997 | (JP) | 9-309875 |
| Oct. 23, 1997 | (JP) | 9-309876 |
| Dec. 16, 1997 | (JP) | 9-363986 |

(51) Int. Cl.[7] ........................ G01N 31/22; G01N 33/52
(52) U.S. Cl. ............................ 422/58; 422/56; 422/57
(58) Field of Search ............................ 422/58, 56, 57, 422/61, 73, 102, 68.1; 436/69, 180, 170, 177

(56) References Cited

U.S. PATENT DOCUMENTS

| | | | | | |
|---|---|---|---|---|---|
| 3,783,696 A | * | 1/1974 | Coleman | ..................... | 73/425 |
| 4,756,884 A | * | 7/1988 | Hillman et al. | ............... | 422/73 |
| 4,917,865 A | * | 4/1990 | Romanauskas | .............. | 422/72 |
| 5,164,598 A | * | 11/1992 | Hillman et al. | ............. | 250/341 |
| 5,885,527 A | * | 3/1999 | Buechler | ..................... | 422/58 |

FOREIGN PATENT DOCUMENTS

| | | | |
|---|---|---|---|
| EP | 0487068 | * | 5/1992 |
| JP | 63-274839 | | 11/1988 |
| JP | 4-188065 | | 7/1992 |
| JP | 9-61310 | | 3/1997 |
| JP | 9-127094 | | 5/1997 |

* cited by examiner

*Primary Examiner*—Jill Warden
*Assistant Examiner*—LaToya Cross
(74) *Attorney, Agent, or Firm*—Finnegan, Henderson, Farabow, Garrett, Dunner, L.L.P.

(57) ABSTRACT

A test device 1 for analyzing a specific component in a test solution with a reagent by allowing the solution introduced via a feed opening 4 to react with the reagent maintained in a predetermined position in a capillary tube 3 having the opening 4 and an air outlet 5. The tube is provided with two hydrophilic regions 31,33 and a hydrophobic region 32. The region 31 transfers the solution from the opening 4 to the reagent. The region 33 is delimited to a predetermined area maintaining the reagent. The region 32 separates the region 31 from the region 33. The reagent and the solution are applied in predetermined amounts to the region 33. A measuring device need not previously measure the solution. The device is useful as an analytical device for rapid and easy analysis, and can be produced in a less number of steps because the reagent can be fixed by merely applying it onto a predetermined position.

4 Claims, 12 Drawing Sheets

TESTING INSTRUMENT FOR ANALYZING LIQUID SAMPLE

This application is a 371 of PCT/JP98/01010 filed of Mar. 11, 1998.

TECHNICAL FIELD

The present invention relates to a test device for analysis of components contained in liquid samples, particularly aqueous solutions such as blood and urine.

BACKGROUND ART

A simple test device for analysis of a liquid sample by reaction with a reagent generally utilizes capillary action for introduction or transfer of a sample to a site for reaction with the reagent in the test device. As this test device, there are the type of device where a reagent applied onto a capillary tube comes to be dissolved in a sample and the type of device where a sample penetrates into a reagent layer provided on a capillary tube.

As an example of the former, JP-A63-274839 describes a test device comprising a lower stretching member also serving as a shaft and an upper member containing a reagent while forming a capillary tube via a spacer with said lower member. As an example of the latter, JP-A 4-188065 describes an analytical device comprising a carrier, a reagent layer sealed to the carrier, and a cover which while covering the reagent layer, is fixed so as to form a capillary chamber with the carrier, said cover having a sample feed opening and an air outlet.

However, in the type of device where a reagent comes to be dissolved in a sample, such as in the test device described in JP-A 63-274839, the concentration of a reaction solution should be accurately defined, so a sample to be fed should previously be introduced into a vessel with a known volume such as pipette. Further, in the type of device where a sample penetrates into a reagent layer, such as in the test device described in JP-A 4-188065, the reagent should be contained in a paper or a film separate from a capillary tube and then fixed to the capillary tube in order to maintain the volume of the reagent layer.

Accordingly, the object of the present invention is to provide a test device which can easily measure a predetermined amount of a sample and simultaneously analyze the sample without pipetting the sample into another vessel or separately preparing a reagent layer for fixing the sample.

DISCLOSURE OF THE INVENTION

To achieve the object, the test device of the present invention is a test device for analyzing a specific component in a test solution with a reagent by allowing the test solution introduced via a test solution feed opening to react with the reagent maintained in a predetermined position in a capillary tube having the feed opening and an air outlet, said capillary tube comprising:

a first hydrophilic region for transferring the test solution from the test solution feed opening to the reagent, a second hydrophilic region having a predetermined area maintaining the reagent, and a hydrophobic region which separates the first hydrophilic region from the second hydrophilic region and communicates with the air outlet without passing through the first and second hydrophilic regions.

According to this test device, a test solution introduced via the test solution feed opening advances by capillary action through the first hydrophilic region to the reagent. Simultaneously, the air in the capillary tube is pushed out and discharged from the air outlet. Once the test solution reaches the hydrophobic region, its transfer is prevented transiently by the hydrophobic region. Then, when external force is applied to the test device, the test solution pass through the hydrophobic region to transfer to the second hydrophilic region.

Because the area of the second hydrophilic region is constant, the amount of the test solution maintained therein is determined by its area and the internal diameter of the capillary tube. When the test solution passes the hydrophobic region to transfer to the second hydrophilic region, the test solution remaining on the hydrophobic region or the solution which cannot be maintained on the second hydrophilic region is removed by repulsion by the hydrophobic region. Accordingly, it is not necessary to pipette the test solution previously into a vessel having a known volume or to maintain the reagent in a layered predetermined area. Further, because the region maintaining the reagent is hydrophilic, the reagent can be fixed to the second hydrophilic region by merely applying it. By reaction between a predetermined amount of the maintained test solution and the reagent, a specific component in the test solution can be analyzed highly accurately.

External force applied to permit the test solution to pass through the hydrophobic region includes e.g. instantaneous vibration or centrifugal force by shaking the test device by the hand of an operator, suction force by suction through the air outlet, and pressurization through the feed opening.

The air outlet is preferably a penetration hole formed in such a direction that it intersects the capillary tube. By forming the penetration hole in this way, the capillary tube can be formed into a tube where excluding the penetration hole, the test solution feed opening only is open, and the overflow of the test solution maintained in the second hydrophilic region can be prevented. The angle at which the penetration hole intersects the capillary tube at the side of the first hydrophilic region is preferably an acute angle. By this constitution, when the test solution is transferred by external force to the second hydrophilic region, it can stop flowing from the penetration hole, thus preventing biohazard.

BEST MODE FOR CARRYING OUT THE INVENTION

First Embodiment

Figure 1:
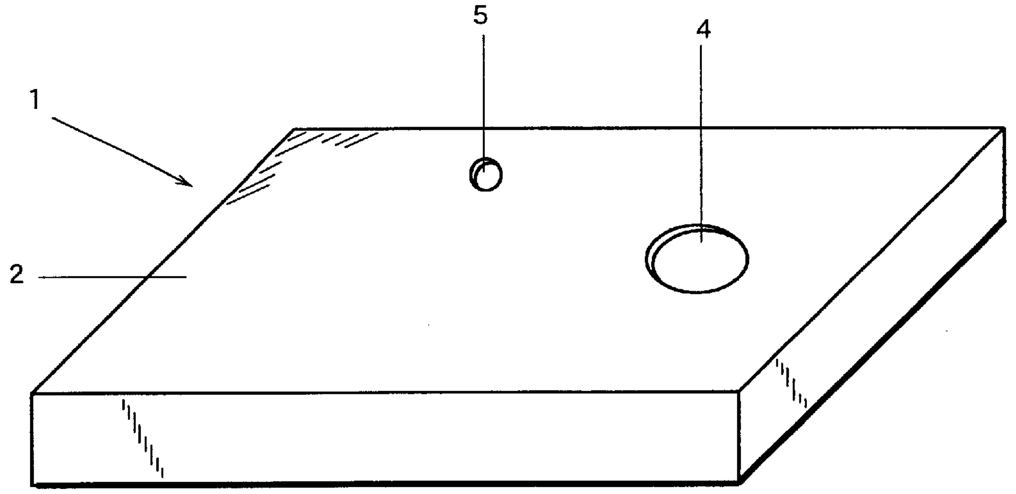
FIG. 1 is a perspective view of the test device in the first embodiment.
Figure 2:
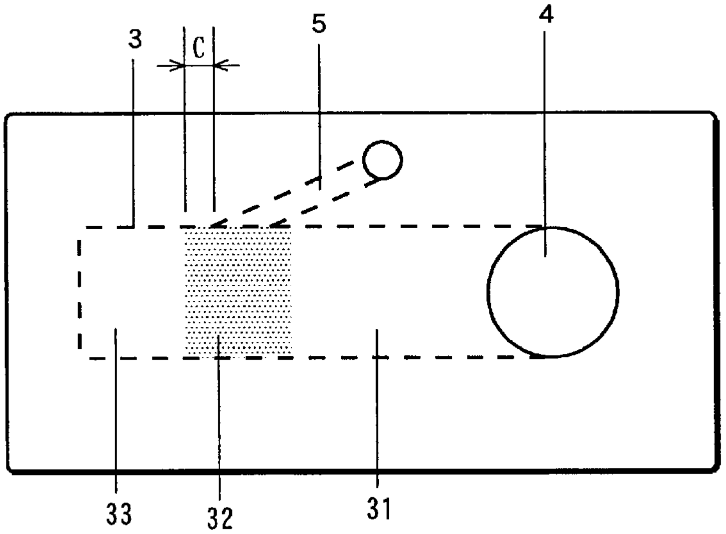
FIG. 2 is a plan view of the test device in the first embodiment.
Figure 3:
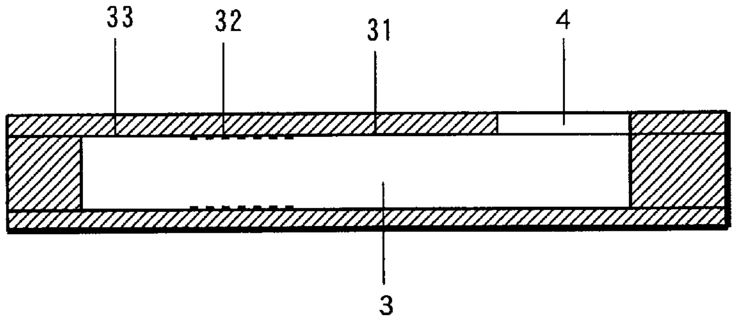
FIG. 3 is a sectional view of the test device in the first embodiment.

The test device of the present invention in the first embodiment is shown in the perspective view of FIG. 1, the plan view of FIG. 2 and the sectional view of FIG. 3.

Test device 1 is provided with rectangular parallelepiped main body 2. The main body 2 is composed of three transparent plates where the middle plate is manufactured into a frame, and the hollow 3 which is long and narrow in the lengthwise direction, surrounded by the frame and the upper and lower plates, functions as a capillary tube. The upper plate in the main body 2 is provided with a feed opening 4 communicating with one end of the hollow 3. The internal surface of the hollow 3 consists of the first hydrophilic region 31 continuous with the feed opening 4 and modified to be hydrophilic, the hydrophobic region 32 continuous therewith, and the second hydrophilic region 33 continuous therewith, and the hollow 3 is blocked at the back of the second hydrophilic region 33. The main body 2 is provided with the penetration hole 5 for permitting the hydrophobic region 32 to communicate with the outside without passing through the hydrophilic regions 31 and 33, and the penetration hole 5 is provided in such a direction that it intersects with the hollow 3 and forms an acute angle with the first hydrophilic region. A reagent (not shown) is applied to the second hydrophilic region 33.

The method of manufacturing the test device 1 is e.g. as follows. Three rectangular plates made of ABS are prepared. ABS is inherently hydrophobic. In the first plate, regions on which the hydrophilic regions 31 & 33 are to be formed are irradiated with UV rays from a low-pressure mercury lamp as a light source. The portions thus irradiated have been modified to be hydrophilic. The second plate is manufactured into a frame and provided with the penetration hole 5. The third plate is provided with the feed opening 4, and the predetermined portions are modified to be hydrophilic in the same manner as in the first plate. After a reagent (not shown) is applied to the second hydrophilic region 33, the three plates are laminated and fixed. The test device is thus completed. Further, a plate made of an originally hydrophilic material may be used in place of the plate made of ABS. In this case, the test device 1 can be produced in the same manner by applying a hydrophobic coating such as alkoxy silane onto the predetermined portions on a hydrophilic plate such as a glass plate. There is no necessity for separately forming a reagent in either case, unlike the prior art.

The procedure of analyzing a liquid sample by the test device 1 is as follows: Collected blood itself or blood subjected to corpuscle-separating treatment, in a slightly larger amount than the optimum amount, is pushed against the feed opening 4. The blood while wetting the first hydrophilic region 31 is transferred by capillary action toward the second hydrophilic region 33, but is prevented from being transferred on the way by the hydrophobic region 32. If collected blood itself is used as a sample, a pretreatment means such as corpuscle separating membrane etc. may be provided on the way of the first hydrophilic region 31. Then, the side of the main body 2 (right side in the drawing) is tapped lightly. By this external force, the blood with which the first hydrophilic region 31 is filled is transferred via the hydrophobic region 32 to the second hydrophilic region 33. Simultaneously, the air in the space surrounded by the second hydrophilic region 33 is removed through the penetration hole 5. The blood initiates reaction with the reagent. The hydrophobic region 32 is not wetted by blood, so the amount of blood to be filled in the second hydrophilic region delimited by the inner wall of the capillary tube and the hydrophobic region 32 is always constant. Accordingly, the blood can be analyzed quantitatively with high accuracy. In addition, the main body 2 is transparent so the blood can be analyzed rapidly with an optical means.

For the following reason, it is preferable that the penetration hole 5 as an air outlet is arranged preferably in a position apart by c=0.2 mm or more from the boundary portion between the secondary hydrophilic region 33 and the hydrophobic region 32. The hydrophobic region, once a test solution is passed therethrough, can be rendered slightly hydrophilic by the action of the test solution. Because the hydrophobic region and the secondary hydrophilic region are continuous on the same surface, a test solution introduced into the second hydrophilic region may form a meniscus at the boundary with the hydrophobic region. Accordingly, if this boundary portion is too close to the air outlet, the meniscus is not stopped by the hydrophobic region and thus binds directly to the air outlet, thus permitting the test solution to flow out through the air outlet.

Second Embodiment

Figure 4:
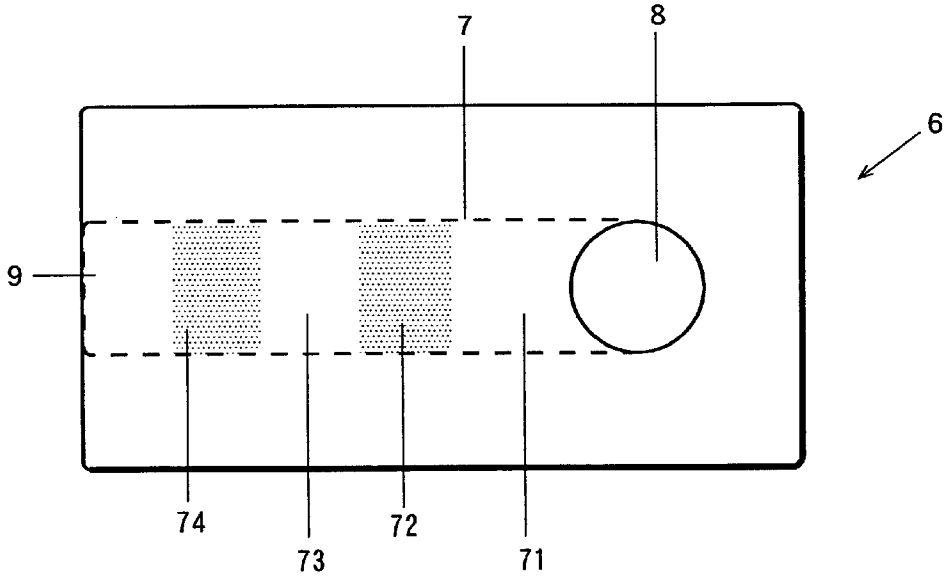
FIG. 4 is a plan view of the test device in the second embodiment.
Figure 5:
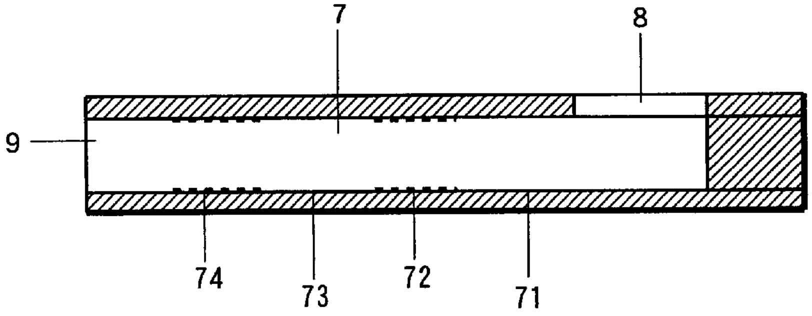
FIG. 5 is a sectional view of the test device in the second embodiment.

Now, the test device in the second embodiment is shown in the plan view of FIG. 4 and in the sectional view of FIG. 5. This test device 6 has the same structure as in the first embodiment except that it is not provided with the penetration hole 5, the hollow 7 is also open in the opposite side to the feed opening 8, the opening 9 has an exhaust function in place of the penetration hole 5, the hydrophobic regions 72 and 74 in the hollow 7 are separated into two positions between which the second hydrophilic region 73 is sandwiched.

In the case of analysis by this test device 6, the air in the hollow 7 is removed through the opening 9 as the test solution advances due to capillary action. The hydrophobic regions 72 and 74 are not wetted by liquid, so the amount of blood filled in the second hydrophilic region 73 delimited by the inner wall of the capillary tube and the hydrophobic regions 72 and 74 is always constant. Because air is removed from the opening 9 which is located at a position extending from the second hydrophilic region 73, the test solution advances rapidly.

Third Embodiment

Figure 6:
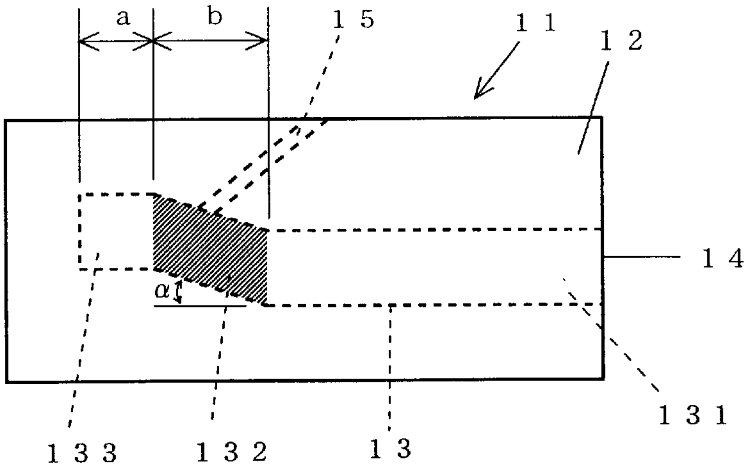
FIG. 6 is a plan view of the test device in the third embodiment.

The test device of the present invention in the third embodiment is shown in the plan view of FIG. 6. In this embodiment, the capillary tube is bent between the first hydrophilic region and the hydrophobic region. Further, assuming that the air outlet extends without bending the first hydrophilic region at the boundary with the hydrophobic region, it is arranged at a position which is not the imaginary extending portion. Hereinafter, the test device is described in detail by reference to the drawings.

The test device 11 is provided with the rectangular parallelepiped main body 12. The main body 12 is composed of three transparent plates, where the middle plate is manufactured into a frame, and the hollow 13 which is long and narrow in the lengthwise direction, surrounded by the frame and the upper and lower plates and bent at two positions, acts as a capillary tube. The hollow 13 begins at one end of the main body 12 and is blocked on the way without reaching the other end. In this example, its beginning portion serves as the feed opening 14.

The inside of the hollow 13 is composed of the first hydrophilic region 131, the hydrophobic region 132, and the second hydrophilic region 133. The first hydrophilic region 131 extends from the feed opening 14 to the first bending portion, the hydrophobic region 132 extends from the first to second bending portions, and the hollow 13 is blocked at the back of the second hydrophilic region 133. The hollow 13 bends to the right at the first bending point and to the left at the second bending point in the direction to which a sample advances. In the present invention, the relationship between the angel of the first bending point, particularly the angle of the outer peripheral side expressed as $\alpha$ in FIG. 1, and the width of the hollow 13 is important. That is, assuming that the first hydrophilic region 131 extends without being bent at the boundary with the hydrophobic region 132, the imaginary extending portion is designed so as to overlap with the second hydrophilic region 133.

The main body 12 is provided with the penetration hole 15 permitting the hydrophobic region 132 to communicate with the outside without passing through both hydrophilic regions 131 and 133. This penetration hole 15 functions as an air outlet. The first bending point is provided at the inner peripheral side with the penetration hole 15. A reagent (not shown) is applied to the second hydrophilic region 133.

The method of manufacturing the test device 11 is essentially the same as in the first embodiment. However, polystyrene (PS) is used in place of ABS as the material.

The procedure of analyzing a test sample by the test device 11 is also the same as in the first embodiment. However, a part of blood flowing from the first hydrophilic region 131 to the secondary hydrophilic region 133 is contacted with the side wall of the hydrophobic region 132. While its direction is changed by the counter force to forcibly transfer the air in the hydrophobic region 132 to the penetration hole 15, the blood is transferred to the second hydrophilic region 133. Accordingly, the air is removed easily as compared with the first embodiment.

The degree of bending of the capillary tube is not limited. The capillary tube may also be bent smoothly or may be bent such that the first hydrophilic region and the hydrophobic region intersect. However, the capillary tube is preferably bend to such an extent that said imaginary extending portion overlaps with the second hydrophilic region. By doing so, the whole of the test solution flowing from the first hydrophilic region is prevented from being splashed on the side wall of the hydrophobic region.

EXAMPLE 1

The test device 11 in the form shown in FIG. 1 was prepared where the width and height of the hollow 13 were 3 mm and 0.2 mm respectively, the depth "a" of the second hydrophilic region 133 was 3 mm, the length "b" of the hydrophobic region 132 was 5 mm, the hollow 13 was bent at 30° to the right at the first bending point and at 30° to the left at the second bending point in the direction to which a sample advances.

Figure 7:
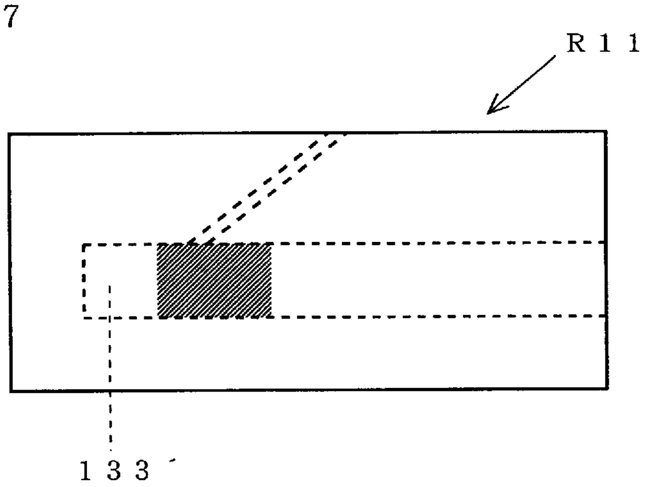
FIG. 7 is a plan view of a test device in a comparative example to the third embodiment.
Figure 8:
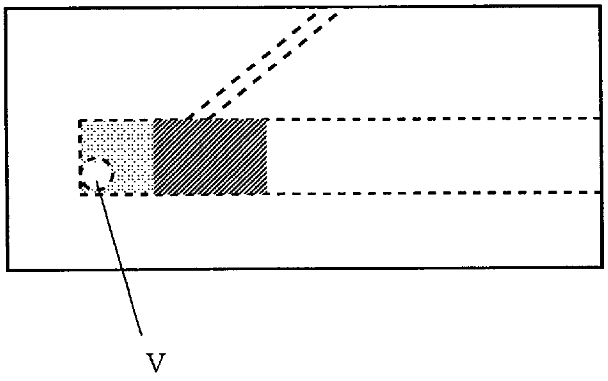
FIG. 8 is a plan view for explaining an evaluation method in Example 1.

Human plasma or serum (hereinafter referred to as human plasma) was introduced as the test solution via the feed opening 14 into the test device 11, and external force was applied to transfer the test solution to the second hydrophilic region 133. For comparison, the test device R11 having the same shape and quality as the test device 11 except that the hollow was not bent as shown in FIG. 7 was prepared, and the test solution was transferred to the second hydrophilic region 133' in the same manner. The ratio of inclusion of air bubble (FIG. 8) in the test solution maintained in the second hydrophilic regions 133 and 133' was evaluated. The number of test devices was 20 for each of the test devices 11 and R11. Three minutes later, the maintained test solution was removed by means of a micro-syringe, and its amount was measured to evaluate the maintenance accuracy. These evaluation results are shown in Table 1.

TABLE 1

(n = 20)

| Test device | Ratio of inclusion of bubble (%) | Maintenance accuracy (CV %) |
|---|---|---|
| 11 | 0 | 2.5 |
| R11 | 25 | 6.1 |

As shown in Table 1, when the test solution is transferred to the reagent-maintaining portion, the test solution can be transferred quantitatively without introducing bubbles into the test solution, according to the test device in this example.

Fourth Embodiment

In the first to third embodiments described above, the hydrophobic region is continuous on the same face with the second hydrophilic region. In this structure, as shown in the first embodiment, the test solution which entered into the second hydrophilic region may form a meniscus in the boundary with the hydrophobic region. If this meniscus is convex, there is no problem. However, if it is concave and the distance "c" (FIG. 2) is unintentionally inadequate, there is a possibility that the test solution goes along the wall of the tube to flow gradually from the air outlet. Accordingly, it becomes difficult to quantitatively maintain the test solution in the second hydrophilic region.

Accordingly, in the fourth embodiment, a groove poorer in wettability than the second hydrophilic region is made at the boundary between the hydrophobic region and the second hydrophilic region. Thus, the groove further stresses the difference in wettability between the two regions to regulate the meniscus. The test device in the fourth embodiment is shown in the plan view of FIG. 9 and in the sectional view of FIG. 10. Hereinafter, the test device is described in detail by reference to the drawings.

The test device 21 is provided with the rectangular parallelepiped main body 22. The main body 22 is composed of three transparent plates, where the middle plate is manufactured into a frame, and the hollow 23 which is long and narrow in the lengthwise direction, surrounded by the frame and the upper and lower plates, acts as a capillary tube. The hollow 23 begins at one end of the main body 22 and is blocked on the way without reaching the other end. In this example, its beginning portion serves as the feed opening 24.

The inside of the hollow 23 is composed of the first hydrophilic region 231, the hydrophobic region 232 and the second hydrophilic region 233 in this order from the side of the feed opening 24. The hollow 23 is blocked at the back of the second hydrophilic region 233. The hollow 23is provided with the grooves 26 facing up and down around the square hydrophobic region 232.

The main body 22 is provided with the penetration hole 25 permitting the hydrophobic region 232 to communicate with the outside without passing through both hydrophilic regions 231 and 233. The penetration hole 25 functions as an air outlet. A reagent (not shown) is applied to the second hydrophilic region 233.

The method of manufacturing the test device 21 is essentially the same as in the first embodiment. However, two plates made of polystyrene (PS) and one plate made of polyvinyl chloride (PVC) are used in place of three plates made of ABS as the material. By irradiation with UV rays, the predetermined regions are modified to be hydrophilic. Then, the grooves 26 are made with a knife around the portion which will form the hydrophobic region 232 on the first and second PS plates. A water-repellent agent such as dimethyl polysiloxane is applied to the portion surrounded by the grooves 26. The presence of the grooves 26 prevents the water-repellent agent from flowing into the hydrophilic region. After a reagent (not shown) is applied to the second hydrophilic region 233, the three plates are laminated and fixed. The test device is thus completed.

The procedure of analyzing a liquid sample by the test device 21 is also the same as shown in the first embodiment. However, the grooves 26 are made at the boundary between the hydrophobic region 232 and the second hydrophilic region 233, so the amount of blood to be filled in the second hydrophilic region 233 is always more constant than in the first embodiment. Accordingly, the sample can be quantitatively analyzed with high accuracy.

Said grooves are made preferably on the whole periphery of the hydrophobic region including the boundary with the second hydrophilic region. The reason for this is as follows: Whether a certain region is hydrophilic or hydrophobic is relatively determined. In the method of altering wettability on a capillary tube, there are cases where a capillary tube is rendered more hydrophilic or more hydrophobic than original. In the present invention, at least two hydrophilic regions and at least one hydrophobic region should be formed in a capillary tube. Accordingly, there are the following 3 combinations: (1) the hydrophobic region remains original while the region to be rendered hydrophilic is modified to be more hydrophilic than original; (2) the region to be rendered hydrophobic is modified to be more hydrophobic than original while the hydrophilic region remains original; and (3) the region to be rendered hydrophobic is modified to be more hydrophobic than original while the region to be rendered hydrophilic is rendered more hydrophilic than original. The modification for conferring hydrophilicity is conducted by physical means such as UV irradiation, whereas the modification for conferring hydrophobicity is usually conducted by applying a water-repellent agent. Said grooves assume the role of preventing the water-repellent agent applied onto the hydrophobic region from flowing to the hydrophilic region. Accordingly, the boundary between the hydrophobic and hydrophilic regions can be made definite by providing the whole periphery of the hydrophobic region with the grooves.

If the diameter of said capillary tube provided with the grooves is 100 to 800 $\mu$m in the depth direction of the groove, the depth of the groove is preferably 1/10 to 1/2 relative to the diameter of the capillary tube.

Fifth Embodiment

Figure 13:
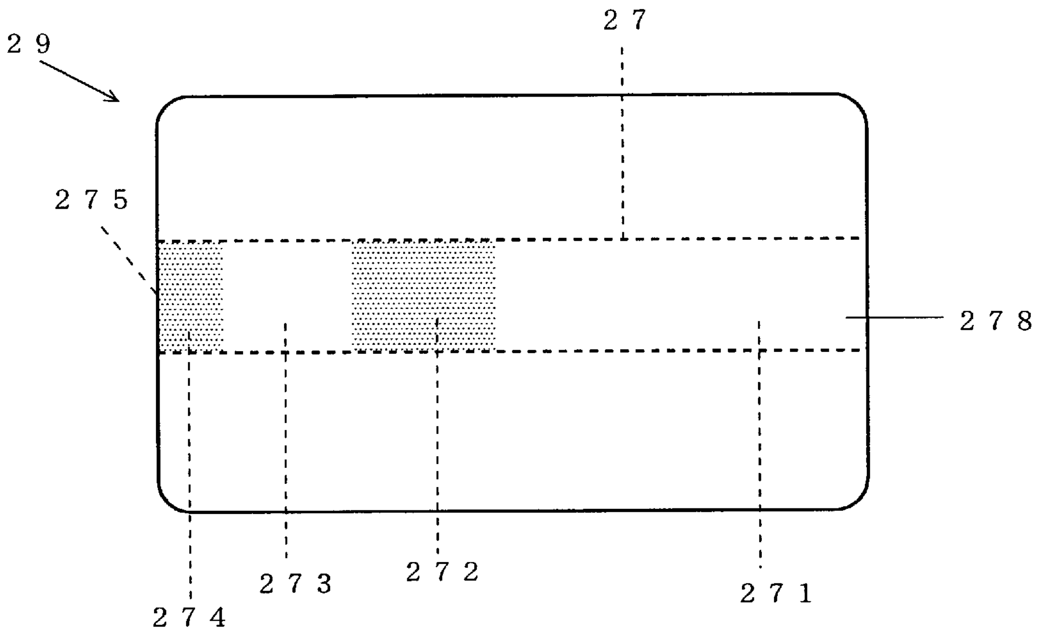
FIG. 13 is a plan view of the test device in the fifth embodiment.
Figure 14:
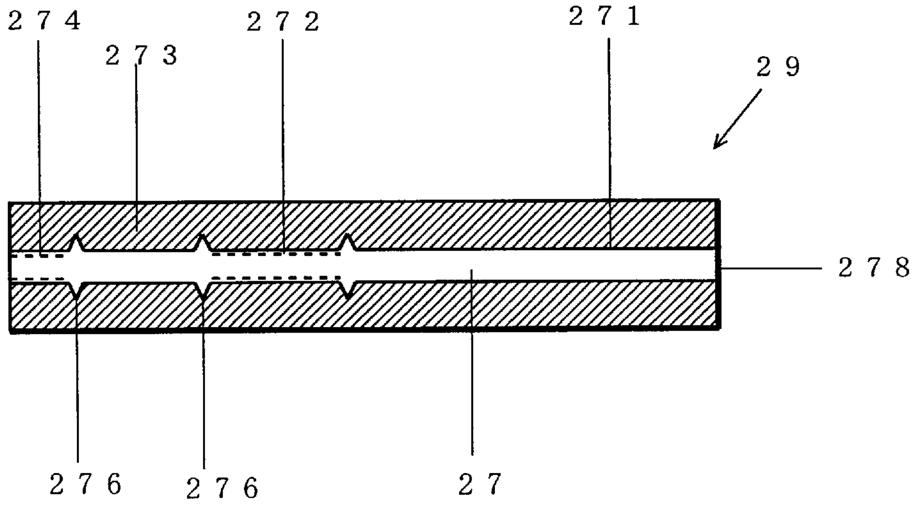
FIG. 14 is a sectional view of the test device in the fifth embodiment.

Now, the test device in the fifth embodiment is shown in the plan view of FIG. 13 and in the sectional view of FIG. 14. The test device 29 has the same structure as in the fourth embodiment except that (1) it is not provided with the penetration hole 25, (2) the hollow 27 is also open in the opposite side to the feed opening 278, and the opening 275 has an exhaust function in place of the penetration hole 25, (3) the hydrophobic regions 272 and 274 in the hollow 27 are separated into two positions between which the second hydrophilic region 273 is sandwiched, and (4) accordingly the groove 262 is also made at the boundary between the second hydrophilic region 273 and the second hydrophobic region 274.

In the case of analysis by this test device 29, the air in the hollow 27 is removed from the opening 275 as a test solution advances due to capillary action. The hydrophobic regions 272 and 274 are not wetted by liquid. Further, the grooves 276 are made in the boundary between the hydrophobic regions 272, 274 and the second hydrophilic region 273, so the amount of blood to be filled in the second hydrophilic region 273 is always constant. Because air is removed from the opening 275 which is located at a position extending from the second hydrophilic region 273, the test solution advances rapidly.

EXAMPLE 2

Figure 9:
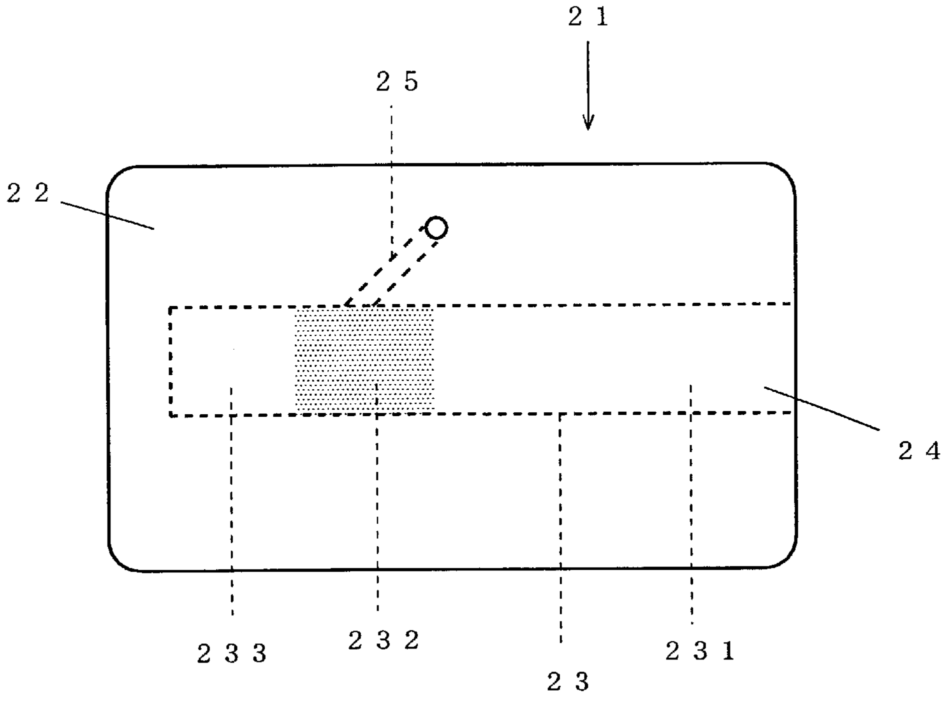
FIG. 9 is a plan view of the test device in the fourth embodiment.
Figure 10:
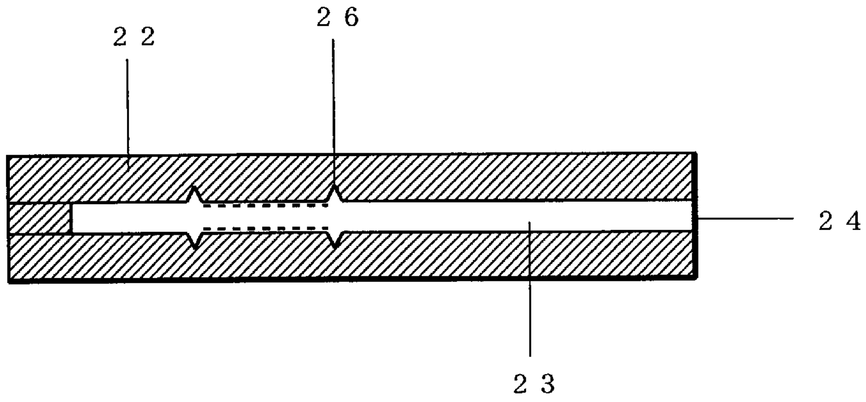
FIG. 10 is a sectional view of the test device in the fourth embodiment.

The test device 21 in the form shown in FIGS. 9 and 10 was prepared where the width and height of the hollow 23 were 3 mm and 500 $\mu$m respectively, the depth of the second hydrophilic region 233 was 3 mm, and the depth of the groove 26 was 130 $\mu$m.

Figure 11:
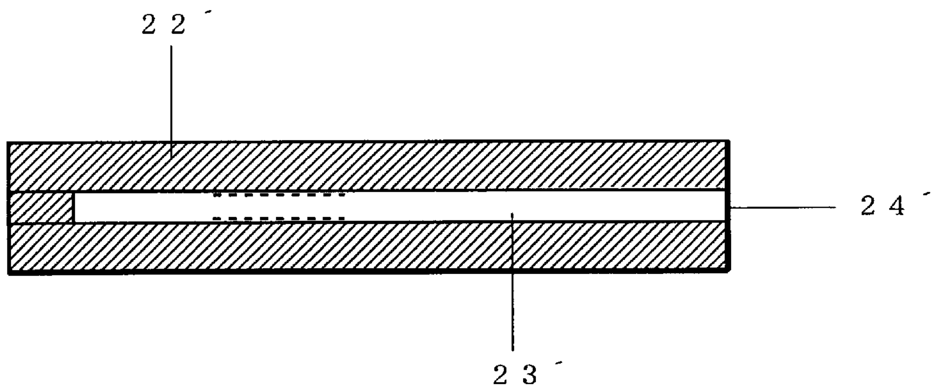
FIG. 11 is a sectional view of a test device in a comparative example to the fourth embodiment.
Figure 12:
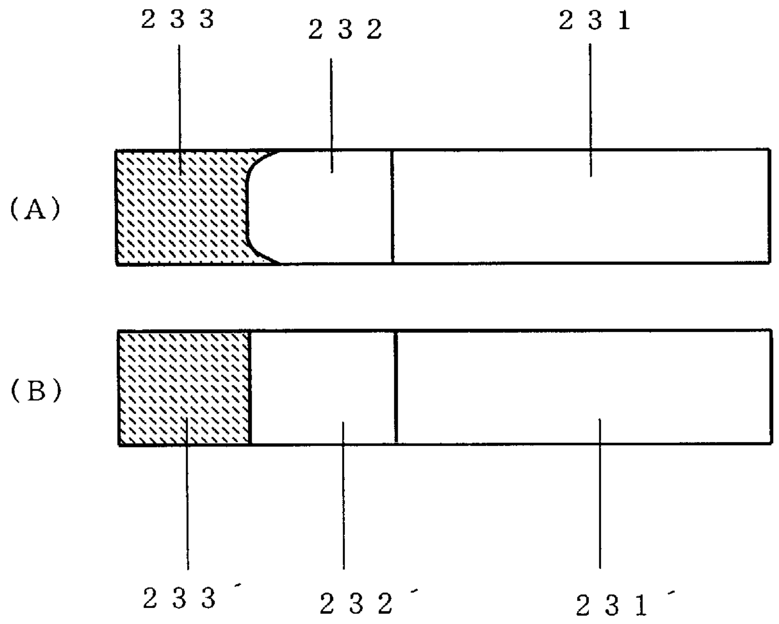
FIG. 12(A) is a plan view of a capillary tube for explaining an evaluation method in Example 2.
FIG. 12(B) is a plan view for a comparative example to Example 2.

Human plasma was introduced as the test solution via the feed opening 24 into the test device 21, and by application of external force, the test solution was transferred to the second hydrophilic region 233. For comparison, the test device 21' having the same shape and quality as the test device 21 except that as shown in FIG. 11, it was not provided with the groove 26 was prepared, and the test solution was transferred to the second hydrophilic region 233' in the same manner. Whether the test solution maintained in the second hydrophilic regions 233 and 233' formed the meniscus shown in FIG. 12(A) or the linear interface shown in FIG. 12(B) in the boundary between the hydrophobic regions 232 and 232' was observed. The number of test devices was 20 for each of the test devices 21 and 21'.

Three minutes later, the maintained test solution was removed by means of a micro-syringe, and its amount was measured to evaluate the maintenance accuracy. These evaluation results are shown in Table 2. In Table 2, the numerical number in item A is the number of test devices forming the meniscus shown in FIG. 12(A), and the numerical number in item B is the number of test devices forming the liner interface shown in FIG. 12(B).

TABLE 2

(n = 20)

| Test device | A | B | Maintenance accuracy (CV %) |
|---|---|---|---|
| 21 | 0 | 20 | 0.9 |
| 21' | 20 | 0 | 3.4 |

As shown in Table 2, when the test solution is transferred to the reagent-maintaining portion, the test solution can be maintained quantitatively without forming a meniscus, according to the test device in this example.

Sixth Embodiment

As described in the fourth embodiment, the test solution introduced into the second hydrophilic region will form a meniscus in the boundary with the hydrophobic region. If this meniscus is large, the test solution cannot be quantitatively maintained in the second hydrophilic region even if the second hydrophilic region is provided with excellent dimension accuracy.

Thus, in the sixth embodiment, the width "d" of the capillary tube in the boundary portion between the hydrophobic region and the second hydrophilic region is made narrower than the width "D" of the capillary tube in the second hydrophilic region. Accordingly, when the area of the second hydrophilic region is constant, the meniscus formed in the test device in this example is smaller than the meniscus formed in the test device with a capillary tube having uniform width. The test device in the sixth embodiment is shown in the plan view of FIG. 15. Hereinafter, the test device is described in detail by reference to the drawings.

The test device 31 is provided with the rectangular parallelepiped main body 32. The main body 32 is composed of three transparent plates, where the middle plate is manufactured into a frame, and the hollow 33 which is long and narrow in the lengthwise direction, surrounded by the frame and the upper and lower plates, acts as a capillary tube. The hollow 33 begins at one end of the main body 32 and is blocked on the way without reaching the other end. In this example, the beginning portion serves as the feed opening 34.

The inside of the hollow 33 is composed of the first hydrophilic region 331, the hydrophobic region 332 and the second hydrophilic region 333 in this order from the side of the feed opening 34. The width of the hollow 33 from the feed opening 34 to the hydrophobic region 332 is constant, whereas the width of the hollow 33 in the second hydrophilic region 333 continuous with the hydrophobic region 332 is increased in the width direction. Then, the hollow 33 is blocked at the back of the second hydrophilic region 333. Accordingly, the first hydrophilic region 331 and the hydrophobic region 332 are rectangular, and the second hydrophilic region 333 only is trapezoid.

The main body 32 is provided with the penetration hole 35 for permitting the hydrophobic region 332 to communicate with the outside without passing through both the hydrophilic regions 331 and 333. The penetration hole 35 is connected to the hydrophobic region 332 in a position apart from the boundary between the hydrophobic region 332 and the second hydrophilic region 333 and extends to the side of the main body 32, so as to be apart from the second hydrophilic region 333. This penetration hole 35 functions as an air outlet. A reagent (not shown) is applied to the second hydrophilic region 333.

The method of manufacturing the test device 31 is essentially the same as in the first embodiment except that PS is used in place of ABS as the material.

The procedure for analyzing a liquid sample by the test device 31 is as shown in the first embodiment.

However, unlike the first embodiment, the width of the boundary portion between the hydrophobic region 332 and the second hydrophilic region 333 is narrower than the width of the second hydrophilic region 333, so the meniscus formed in the boundary portion is small. Accordingly, the amount of blood to be filled in the second hydrophilic region 333 is always more constant than in the first embodiment, and thus the blood can be analyzed quantitatively with high accuracy.

Said air outlet is arranged preferably at a position apart by c=0.2 mm or more from the boundary portion between the secondary hydrophilic region and the hydrophobic region. By doing so, the meniscus is certainly stopped by the hydrophobic region without binding directly to the air outlet, as mentioned in the first embodiment. As a result, the outflow of the test solution through the air outlet is prevented.

Seventh Embodiment

Figure 18:
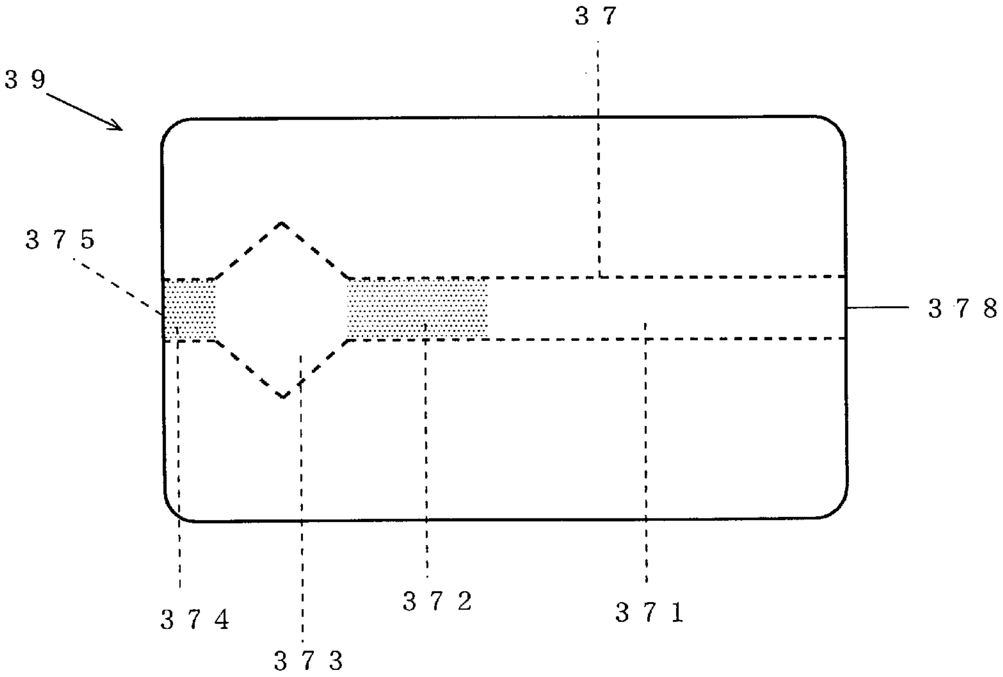
FIG. 18 is a plan view of the test device in the seventh embodiment.

Now, the test device in the seventh embodiment is shown in the plan view of FIG. 18. This test device 39 has the same structure as in the sixth embodiment except that (1) it is not provided with the penetration hole 35, (2) the hollow 37 is also open in the opposite side to the feed opening 378, and the opening 375 has an exhaust function in place of the penetration hole 35, (3) the hydrophobic regions 372 and 374 in the hollow 37 are separated into two positions between which the second hydrophilic region 373 is sandwiched, and (4) accordingly the width of the capillary tube at the boundary portion between the second hydrophilic region 373 and the second hydrophobic region 374 is narrower than the width of the capillary tube in the second hydrophilic region 373.

In the case of analysis by the test device 39, the air in the hollow 37 is removed from the opening as the test solution advances due to capillary action. The hydrophobic regions 372 and 374 are not wetted by liquid. In addition, the width of the boundary portion between the hydrophobic regions 372, 374 and the second hydrophilic region 373 is narrow, so the amount of blood filled in the second hydrophilic region 373 is always constant. Because air is removed from the opening 375 which is located at a position extending from the second hydrophilic region 373, the test solution advances rapidly.

EXAMPLE 3

Figure 15:
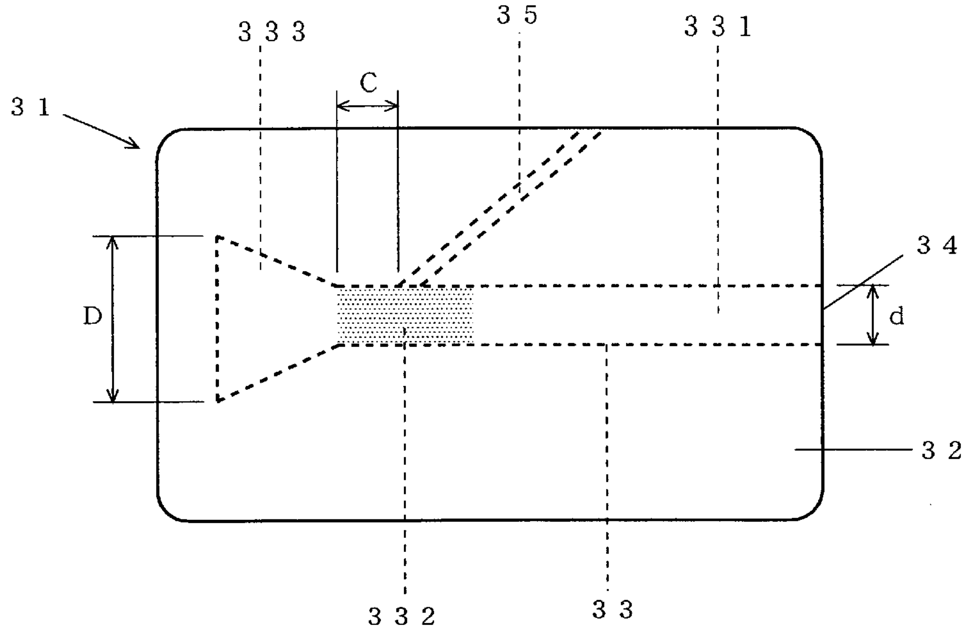
FIG. 15 is a plan view of the test device in the sixth embodiment.

The test device 31 in the form shown in FIG. 15 was prepared where the width "d" and the height of the hollow 33 from the feed opening 34 to the second hydrophilic region 333 were 3 mm and 500 μm respectively, the depth of the second hydrophilic region 333 was 3 mm, and the maximum width "D" of the second hydrophilic region 333 was 5 mm. The penetration hole 35 was arranged in a position apart by 2 mm from the boundary portion between the hydrophobic region 332 and the second hydrophilic region 333.

Figure 16:
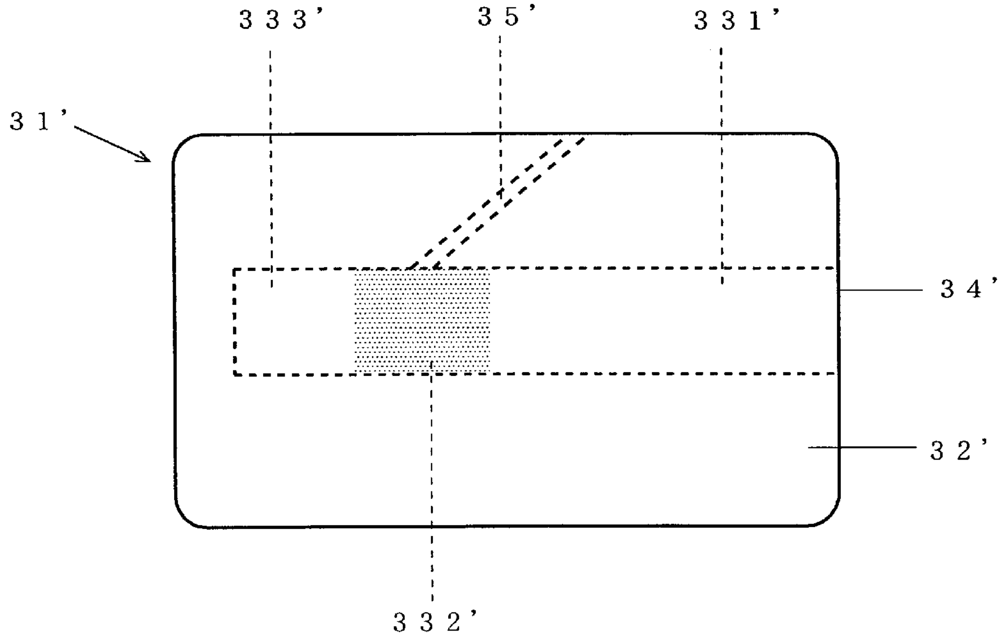
FIG. 16 is a plan view of a test device in a comparative example to the sixth embodiment.
Figure 17:
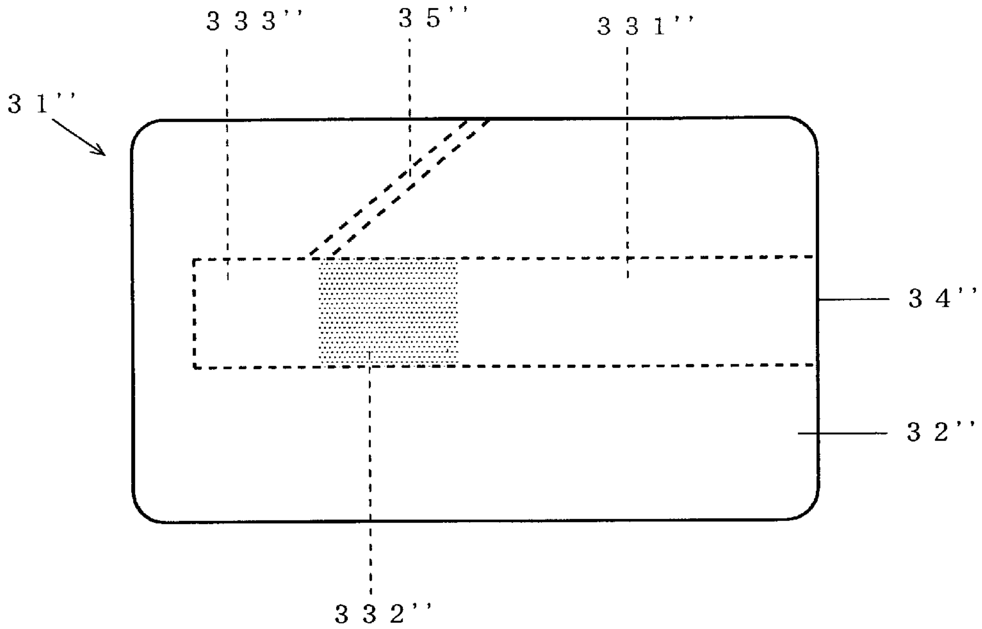
FIG. 17 is a plan view of a test device in another comparative example to the sixth embodiment.

Human plasma was introduced as a test solution via the feed opening 34 to this test device 31, and by applying external force, the test solution was transferred to the second hydrophilic region 333. For comparison, the test device 31' having the same shape and quality as the test device 31 except that the width of the hollow 33 is equally 3 mm as shown in FIG. 16 was produced, and the test solution was transferred in the same manner to the second hydrophilic region 333'. Further, the test device 31" having the same shape and quality as the test device 31' except that as shown in FIG. 17, the penetration hole is formed at the boundary region between the hydrophobic region 332 and the second hydrophilic region 333 was produced, and the test solution was transferred in the same manner to the second hydrophilic region 333". The number of devices was 20 for each of the test devices 31, 31' and 31".

Three minutes later, the test solution maintained in the second hydrophilic region in each device was removed by means of a micro-syringe, and its amount was measured to evaluate the maintenance accuracy. These evaluation results are shown in Table 3.

TABLE 3

(n = 20)

| Test device | Maintenance accuracy (CV %) |
|---|---|
| 31 | 2.1 |
| 31' | 3.4 |
| 31" | 5.7 |

As shown in Table 3, when the test solution is transferred to the reagent-maintaining portion, the test solution can be maintained quantitatively without forming a meniscus, according to the test device in this example. On the other hand, the test devices 31' and 31" were inferior in maintenance accuracy. The amount of the sample maintained in the test device 31' varied probably because of a varying size of the meniscus. The amount of the sample maintained in the test device 31" varied probably because a small amount of the test solution leaked from the penetration hole 35" before the test solution was removed from the second hydrophilic region 333".

Eighth Embodiment

Because the area of the second hydrophilic region is constant, the amount of the test solution maintained in the second hydrophilic region is approximately determined by its area and the internal diameter of the capillary tube. However, when the test solution is transferred via the hydrophobic region to the second hydrophilic region, an excess test solution remains on the hydrophobic region or the first hydrophilic region. If this excess solution is left, it binds to the test solution maintained in the second hydrophilic region, thus lowering analytical accuracy.

Accordingly, in the eighth embodiment, an excess liquid-retainer capable of retaining the test solution that may flow from the second hydrophilic region is formed in the hydrophobic region ranging from the boundary portion between the hydrophobic region and the second hydrophilic region to the air outlet. In this embodiment, an excess solution is transiently retained in the liquid retainer formed in the hydrophobic region. Because this portion is hydrophobic, it repels an excess test solution into the air outlet. Accordingly, the test solution can be analyzed highly accurately. The air outlet is preferably rendered more readily wetted with the test solution than in the hydrophobic region. By doing so, an excess test solution retained in the liquid retainer can be rapidly removed into the air outlet. The test device in the eighth embodiment is shown in the plan view of FIG. 19. Hereinafter, the test device is described in detail by reference to the drawings.

The test device 41 is provided with the rectangular parallelepiped main body 42. The main body 42 is composed of three transparent plates where the middle plate is manufactured into a frame, and the hollow 43 which is long and narrow in the lengthwise direction, surrounded by the frame and the upper and lower plates, acts as a capillary tube. The hollow 43 begins at one end of the main body 42 and is blocked on the way without reaching the other end. In this example, the beginning portion serves as the feed opening 44.

The inside of the hollow 43 is composed of the first hydrophilic region 431, the hydrophobic region 432 and the second hydrophilic region 433 in this order from the side of the feed opening 44. The width of the hollow 43 from the feed opening 44 to an approximately central region in the hydrophobic region 432 is constant, whereas the width of the hollow 43 in the remainder of the hydrophobic region 432 spreads at one side in the width direction. This spreading portion serves as the liquid retainer 47. The hollow 43 in the second hydrophilic region 433 has the same width as that of the feed opening 44 and is blocked at its back.

The main body 42 is provided with the penetration hole 45 for permitting the hydrophobic region 432 communicate with the outside without passing through both the hydrophilic regions 431 and 433. The penetration hole 45 is connected to the liquid retainer 47 at a portion apart from the boundary between the hydrophobic region 432 and the second hydrophilic region 433 and extends to the side of the main body 42, so as to be apart from the second hydrophilic region 433. The penetration hole 45 functions as an air outlet. A reagent (not shown) is applied to the second hydrophilic region 433.

The method of manufacturing the test device 41 is the same as in the first embodiment except that two plates made of PS and one plate made of PVC are used in place of plates made of ABS as the material.

The procedure for analyzing a liquid sample by the test device 41 is also the same as in the first embodiment.

However, unlike the first embodiment, an excess test solution which cannot be maintained in the second hydrophilic region 433 is retained transiently in the liquid retainer 47. Since the liquid retainer 47 is hydrophobic, the excess solution is immediately repelled by the liquid retainer 47, thus flowing into the penetration hole 45 which is less hydrophobic than the liquid retainer 47. Accordingly, the amount of blood to be filled in the second hydrophilic region 433 is always more constant than in the first embodiment, and the sample can be analyzed quantitatively with high accuracy.

EXAMPLE 4

Figure 19:
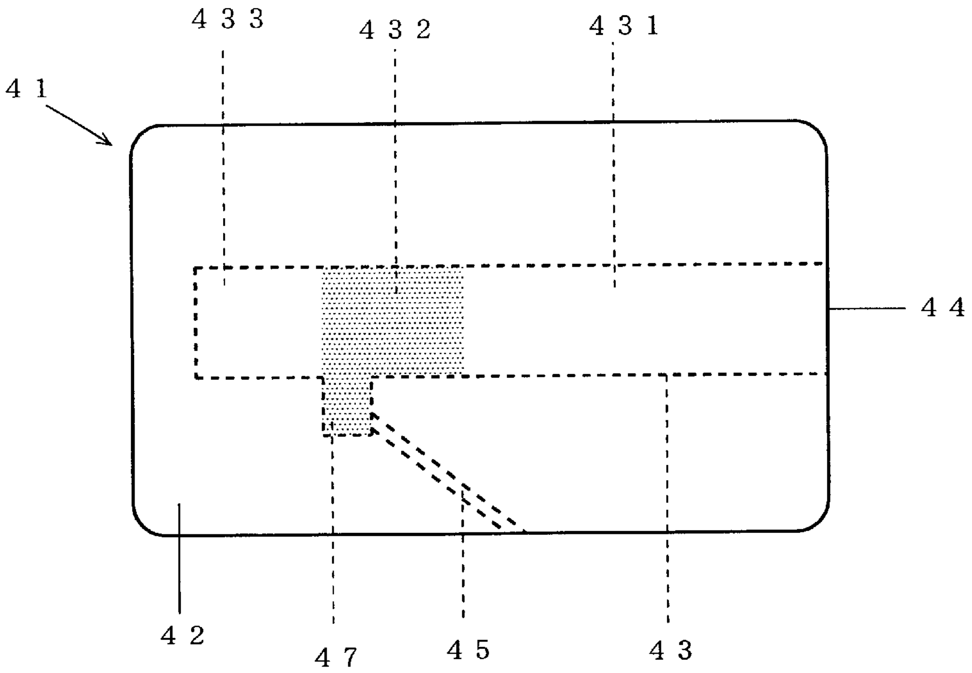
FIG. 19 is a plan view of the test device in the eighth embodiment.

The test device 41 in the form shown in FIG. 19 was prepared where the width and height of the hollow 43 were 3 mm and 500 μm respectively, and the depth of the second hydrophilic region 433 was 3 mm.

Human plasma was introduced as the test solution via the feed opening 44 into the test device 41, and by applying external forces, the test solution was transferred to the second hydrophilic region 433. For comparison, the test device (not shown) having the same shape and quality as the test device 41 except that it was not provided with the liquid retainer 47 was prepared, and the test solution was transferred to the second hydrophilic region in the same manner. Three minutes later, the maintained test solution was removed by means of a micro-syringe, and its amount was measured to evaluate the maintenance accuracy. These evaluation results are shown in Table 1. The number of test devices for each case was 20.

TABLE 4

| Test device | Maintenance accuracy (CV %) (n = 20) |
|---|---|
| 41 | 1.8 |
| Comparative device | 3.4 |

As shown in Table 4, when the test solution is transferred to the reagent-maintaining portion, an excess test solution can be removed rapidly and a suitable amount of the test solution only is maintained according to the test device in this example.

Ninth Embodiment

In the ninth embodiment, an excess test solution which could not be maintained in the second hydrophilic region is removed in a different constitution from that in the eighth embodiment. In this embodiment, the air outlets are formed at a position (first air outlet) close to the first hydrophilic region at one side of the capillary tube and at a position (second air outlet) close to the second hydrophilic region at the other side of the capillary tube respectively, between which the hydrophobic region is sandwiched. The inside of the capillary tube communicates with the air via the first air outlet, so an excess test solution is rapidly captured by the second air outlet. Accordingly, it can be analyzed highly accurately. The test device in the ninth embodiment is shown in the plan view of FIG. 20. Hereinafter, the test device is described in detail by reference to the drawings.

The test device 51 is provided with the rectangular parallelepiped main body 52. The main body 52 is composed of three transparent plates where the middle plate is manufactured into a frame, and the hollow 53 which is long and narrow in the lengthwise direction, surrounded by the frame and the upper and lower plates, acts as a capillary tube. The hollow 53 begins at one end of the main body 52 and is blocked on the way without reaching the other end. In this example, the beginning portion serves as the feed opening 54.

The inside of the hollow 53 is composed of the first hydrophilic region 531, the hydrophobic region 532 and the second hydrophilic region 533 in this order from the side of the feed opening 54. The hollow 53 is blocked at the back of the second hydrophilic region 533, and possesses uniform width from the feed opening 54 to the blocked portion.

The main body 52 is provided with the penetration holes 55 and 58 for permitting the hydrophobic region 532 to communicate with the outside without passing through both the hydrophilic regions 531 and 533. These penetration holes 55 and 58 function as an air outlets. The penetration holes 55 and 58 are formed at both sides of the capillary tube such that they face to each other around the hydrophobic region 532. However, the penetration hole 55 is close to the second hydrophilic region 533, and the penetration hole 58 is close to the first hydrophilic region. The inside of the penetration hole 58 has the same hydrophobicity as the hydrophobic region 532, while the inside of the penetration hole 55 is rendered less hydrophilic than the second hydrophilic region 533 but more hydrophilic than the hydrophobic region 532. A reagent (not shown) is applied to the second hydrophilic region 533.

The method of manufacturing the test device 51 is the same as in the first embodiment except that two plates made of PS and one plate made of PVC are used in place of plates made of ABS as the material.

The procedure for analyzing a liquid sample by the test device 51 is also the same in the first embodiment.

However, in the test device 51 unlike the first embodiment, air is introduced via the penetration hole 58 while an excess test solution is removed from the penetration hole 55 relatively poor in hydrophobicity. Accordingly, the amount of blood to be filled in the second hydrophilic region 533 is always more constant than in the first embodiment, and the sample can be analyzed quantitatively with high accuracy.

The second air outlet also functions in capturing an excess test solution, whereas the first air outlet always fulfills the exhaust function only. Accordingly, the inside of the first air outlet is preferably rendered more hydrophobic than the inside of the second air outlet in order to raise the reliability of the first air outlet.

EXAMPLE 5

Figure 20:
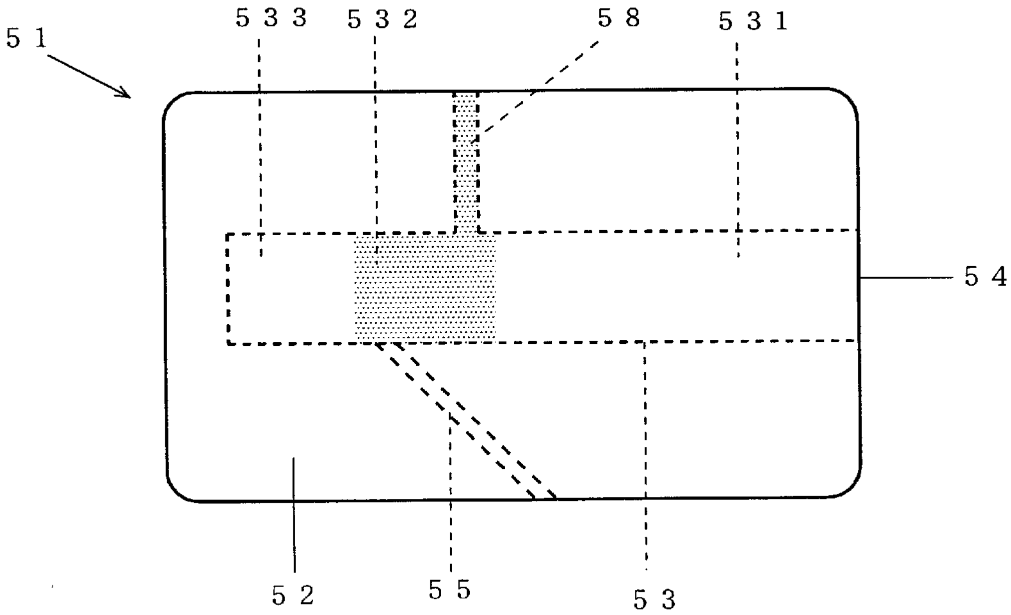
FIG. 20 is a plan view of the test device in the ninth embodiment.

The test device 51 in the form shown in FIG. 20 was prepared where the width and height of the hollow 53 were 3 mm and 500 μm respectively, and the depth of the second hydrophilic region 533 was 3 mm.

Human plasma was introduced as the test solution via the feed opening 54 into the test device 51, and by applying external forces, the test solution was transferred to the second hydrophilic region 533. For comparison, the test devices R1, R2 and R3 (not shown) having the same shape and quality as those of the test device 51 except for the following differences were produced besides the test device 51. The test device R1 does not have the penetration hole 58, and further the inside of the penetration hole 55 is rendered hydrophobic to the same degree as in the hydrophobic region 532. In the test device R2, the insides of the penetration holes 55 and 58 are rendered hydrophobic to the same degree as in the hydrophobic region 532. In the test device R3, the inside of the penetration hole 55 is rendered hydrophobic to the same degree as in the hydrophobic region 532, while the inside of the penetration hole 58 is rendered hydrophilic. In the test devices R1 to R3, the test solution was transferred to the second hydrophilic region in the same manner.

Figure 21:
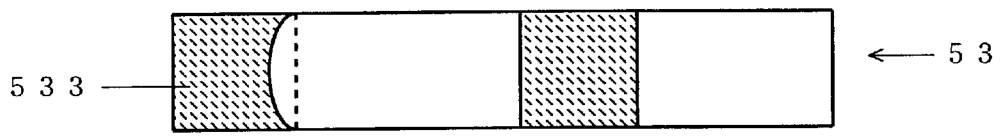
FIG. 21 is a plan view of a first type of transfer of a test solution in a capillary tube.
Figure 22:
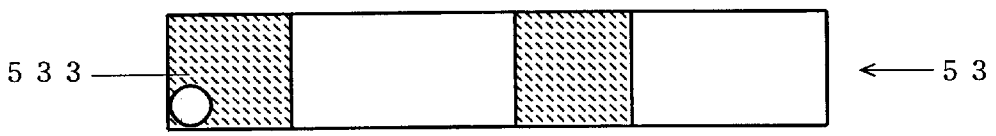
FIG. 22 is a plan view of a second type of transfer of a test solution in a capillary tube.
Figure 23:
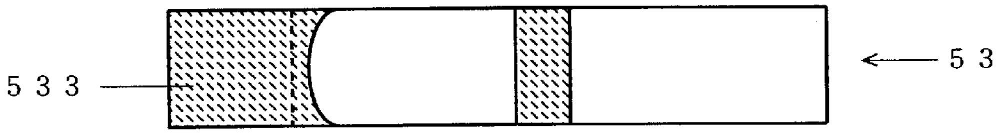
FIG. 23 is a plan view of a third type of transfer of a test solution in a capillary tube.

When transfer of the test solution was observed, the following three types of abnormal transfer occurred besides the normal transfer of a suitable amount of the test solution to be maintained in the second hydrophilic region. In the first type, the amount of the solution transferred to the second hydrophilic region was inadequate as shown in FIG. 21. In the case of the second type, the test solution retained in the second hydrophilic region contained bubbles as shown in FIG. 22. These problems in both cases were possibly due to an insufficient exhaust function at the time of transfer of the test solution. In the case of the third type, an excess test solution remained in the hydrophobic region as shown in FIG. 23. The number of test devices showing such abnormal transfer is shown for each type in Table. 5.

Three minutes later, the maintained test solution was removed by means of a micro-syringe, and its amount was measured to evaluate the maintenance accuracy. These evaluation results are collectively shown in Table 5. The number of test devices for each case was 20.

TABLE 5

| Test device | FIG. 21 | FIG. 22 | FIG. 23 | Maintenance accuracy (CV %) (n = 20) |
|---|---|---|---|---|
| R1 | 2 | 4 | 4 | 4.7 |
| R2 | 0 | 3 | 3 | 4.0 |

TABLE 5-continued (n = 20)

| Test device | FIG. 21 | FIG. 22 | FIG. 23 | Maintenance accuracy (CV %) |
|---|---|---|---|---|
| R3 | 0 | 2 | 2 | 2.8 |
| 41 | 0 | 1 | 0 | 1.2 |

As shown in Table 5, when the test solution is transferred to the reagent-maintaining portion, an excess test solution is rapidly removed and a suitable amount of the test solution only is maintained without forming bubbles, according to the test device in this example.

Tenth Embodiment

The suction force by capillary action is not strong and readily affected by the physical properties of the liquid. Accordingly, if the transfer of the test solution depends exclusively on capillary action, the transfer of the test solution to the analytical part is time-consuming. Further, the distance between the test solution feed opening and the analytical part cannot be made large.

Figure 24:
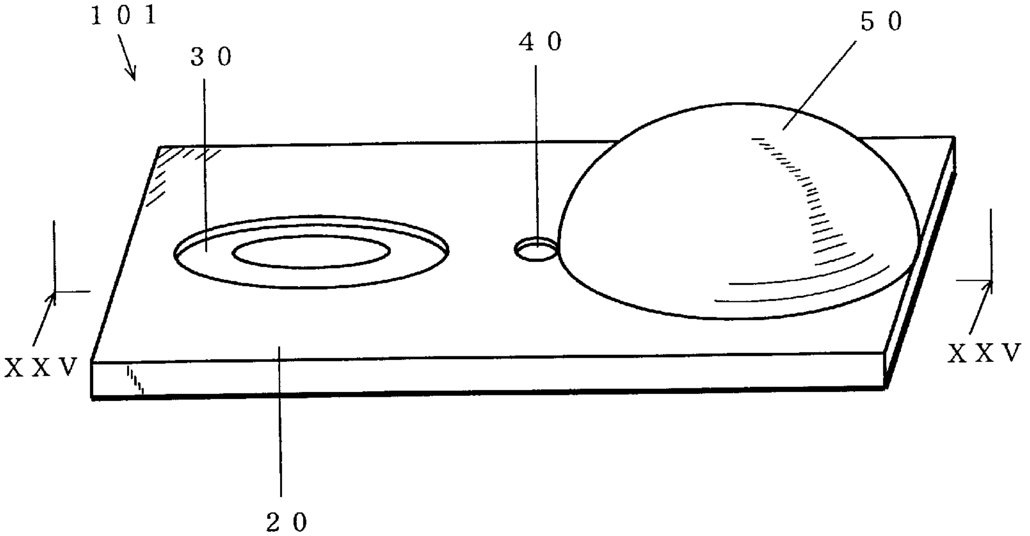
FIG. 24 is a perspective view of the test device in the tenth embodiment.
Figure 25:
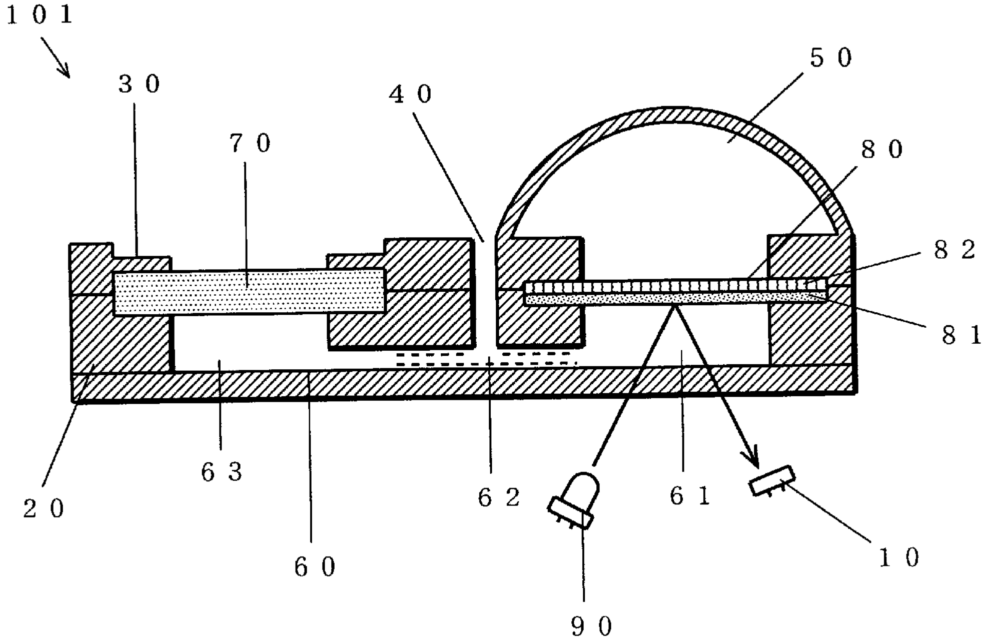
FIG. 25 is a sectional view in XXV—XXV of FIG. 24.

Accordingly, the test device in the tenth embodiment is provided with a suction generating means for promoting transfer of the test solution. FIG. 24 is a perspective view of the test device in the tenth embodiment, and FIG. 25 is an XXV—XXV sectional view of FIG. 24.

The test device 101 is provided with the rectangular parallelepiped main body 20, and the main face of the main body 20 is provided with the test solution feed opening 30, the air hole 40, and the suction generating chamber 50. The suction generating chamber 50 is arranged so as to be protruded from the main face of the main body 20, and its inside is hollow. As shown in FIG. 25, the inside of the test device 101 is provided with the capillary tube 60 leading from the test feed opening 30 to the suction generating chamber 50. The capillary tube 60 communicates on the way with the air via the air hole 40. Both ends of the capillary tube 60 are blocked by the corpuscle removing filter 70 at the side of the test solution feed opening 30 and by the reagent film 80 at the side of the suction generating chamber 50. In the inside of the capillary tube 60, the analytical part 61 as the first hydrophilic region, the hydrophobic region 62, and the second hydrophilic region 63 are formed linearly from the side of the suction generating chamber 50 to the side of the feed opening 30. Said air hole 40 is formed in the hydrophobic region 62.

The materials of the main body 20 make use of light-transmissible plastics. For example, ABS, polystyrene, polyethylene, polyvinyl chloride, polyethylene terephthalate (PET) etc. are used.

The materials of the suction generating chamber 50 should be elastic so as to change the volume of the chamber. The materials which can be used for the suction generating chamber 50 include rubber, polyethylene, polyvinyl chloride, PET etc.

The corpuscle removing filter 70 makes use of matrix such as glass filter to impart liquid permeability and solid impermeability. Lecithin may be used as filter medium to improve the ability to remove corpuscle components.

The reagent film 80 should be gas-permeable and simultaneously liquid-impermeable. Accordingly, a porous resin is used as the reagent film 80. Further, the reagent film 80 contains a reagent for analyzing a specific component, as well as an optically reflective agent such as titanium dioxide. Then, the lower half of the reagent film 80 is formed into the reagent layer 81 containing the reagent, and the upper half thereof is formed into the optically reflective layer 82 containing an optically reflective agent. However, the reagent and the optically reflective agent may be mixed.

The method of forming the analytical part 61 (first hydrophilic region), the hydrophobic region 62, and the second hydrophilic region 63 in the inside of the capillary tube 60 is essentially the same as in the first embodiment.

Analysis of plasma or serum components by the test device 101 is as follows.

First, after whole blood is applied onto the feed opening 30, the suction generating chamber 50 is pressed with a finger whereby its volume is reduced, and simultaneously the excess air therein is removed from the air hole 40. Then, the air hole 40 is closed with another finger, and the finger pressing against the suction generating chamber 50 is removed. The suction generating chamber 50 is composed of an elastic material so that the reduced volume will return to the original volume. Suction is thereby generated, and the whole blood in the feed opening 30 is introduced into the capillary tube 60, to transfer to the analytical part 61. However, the corpuscle removing filter 70 allows the liquid to pass but does not allow solids to pass therethrough, so the corpuscle components are removed and only plasma or serum is introduced into the capillary tube 60, to transfer to the analytical part 61. Because this filter is arranged apart from the analytical part, there is no need to worry about errors due to the influence of corpuscle components in order to optically measure the result of reaction with the reagent.

Then, the finger with which the air hole 40 is closed is removed and left for a while. By doing so, a predetermined amount of plasma or serum can be fed to the analytical part 61. That is, the analytical part 61 is hydrophilic, and it is surrounded by the hydrophobic region 62 and the air-permeable but liquid-impermeable reagent film 80, so the amount of plasma or serum fed to the analytical part 61 is always equal to the volume of the analytical part 61. However, because the suction force of the suction generating chamber 50 is relatively strong where the ability of the hydrophobic region 62 to repel water is inadequate, excess plasma or serum may remain in the hydrophobic region 62. In this case, the test device 101 is e.g. slightly shaken with the hand so that the excess plasma or serum may be returned to the second hydrophilic region 63. If there is air in the capillary tube 60, the air is simultaneously removed from the air hole 40.

If plasma or serum is fed to the analytical part 61, the reagent contained in the reagent film 80 is eluted. As a result of its reaction with a specific component in plasma or serum, a colored substance is formed and the plasma or serum is thereby colored. The main body 20 is light-transmissible, and the reagent film 80 has the optically reflective layer 82, so the degree of this coloration can be measured with a device equipped with light irradiation part 90 and light detecting part 10, such as densitometer.

The test device 101 can generate strong suction in the capillary tube by the suction generating means in addition to capillary action, and this forcible suction can be utilized to transfer the test solution forcibly from the feed opening for the test solution to the analytical part.

Accordingly, unlike a test device using only capillary action, a test solution containing corpuscles such as whole blood which require filtration can also be measured by the present test device, and the test solution can be rapidly transferred. Further, even a test solution obtained in such a small volume as the volume of the analytical part can be subjected to measurement. That is, regardless of the amount or physical properties, the test solution can be certainly transferred to the analytical part.

Eleventh Embodiment

Figure 26A:
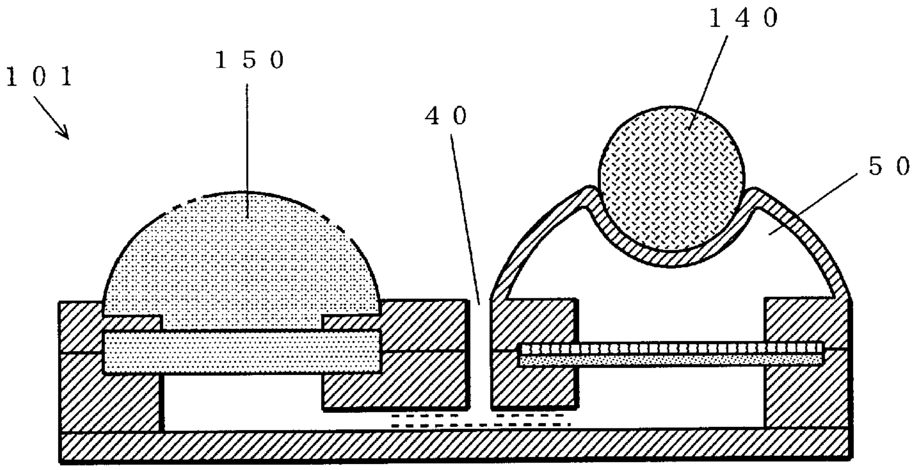
FIGS. 26(A), (B) and (C) are sectional views of the test device at the preparative stage, corpuscle removing stage and plasma volume regulating stage respectively in the eleventh embodiment.
Figure 26B:
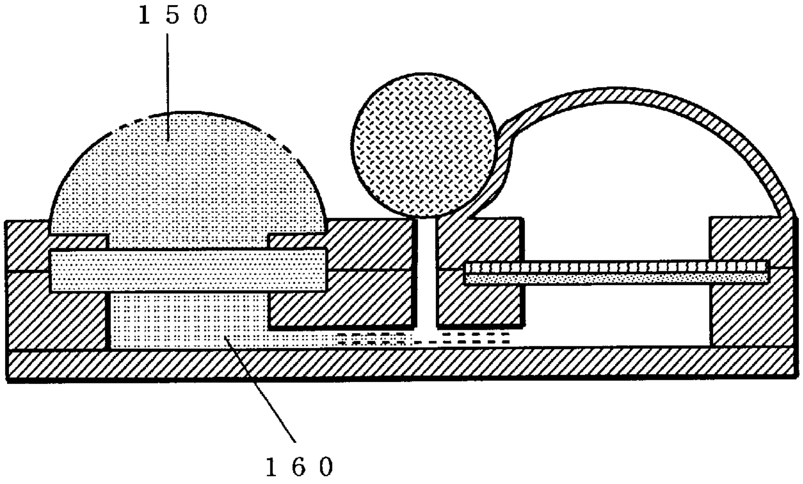
Figure 26C:
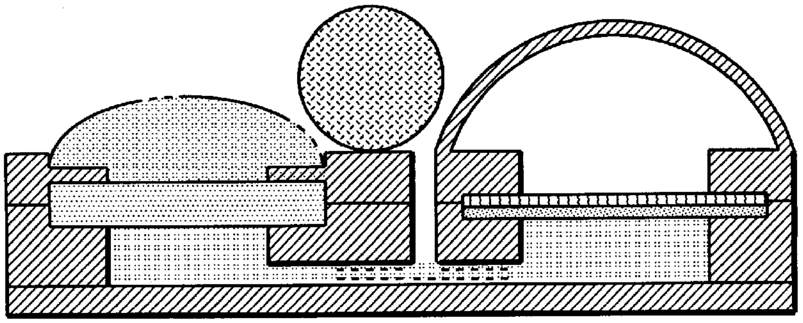

As the eleventh embodiment, the test device 101 including a roller automatically regulating the volume of the suction generating chamber and opening and shutting the air hole is shown in FIG. 26. FIG. 26 shows the test device at each stage for analysis of plasma or serum components. FIG. 26(A), FIG. 26(B), and FIG. 26(C) are sectional views of the test device 11 at the preparative stage, corpuscle removing stage and plasma or serum volume regulating stage.

At the preparative stage (A), roller 140 presses the suction generating chamber 50 downward to reduce the volume. At the stage of (B), roller 140 rolls down from the suction generating chamber 50 and stops on the air hole 40, thereby shutting the passage of air. The volume of the suction generating chamber 50 will be returned to the original volume, thus generating suction. Corpuscles are thereby removed from whole blood 150, and plasma or serum 160 is introduced into the capillary tube. At the stage of (C), roller 140 rolls again whereby the air hole 40 is opened. At this stage, the amount of plasma or serum fed to the analytical part is regulated.

Because roller 140 automatically works, it is not necessary for the operator to press the suction generating chamber 50 or to close the air hole 40 by the finger. Accordingly, the procedure is made simpler, and an operational miss by the operator can be prevented.

In the tenth and eleventh embodiments, the reagent film 80 contains a reagent, but the reagent may replaced by the air-permeable but liquid-impermeable film and the reagent may be directly applied onto the surface of its facing analytical part 61, i.e. onto the surface of the first hydrophilic region in order to fix the reagent thereto.

Industrial Applicability

According to the test device of the present invention, a test solution can be analyzed by applying a suitable amount of a test solution without previously measuring the test solution by a measuring device. Accordingly, it is useful as an analytical device for rapid and easy analysis. Further, the test device of the preset invention can be produced in a less number of steps because a reagent can be fixed by merely applying the reagent onto a predetermined position.

What is claimed is:

1. A test device for analyzing a specific component in a test solution with a reagent by allowing the test solution introduced via a test solution feed opening to react with the reagent maintained in a predetermined position in a capillary tube having the feed opening and an air outlet, said test device comprising:

a gas-permeable, liquid-impermeable film blocking an end at the opposite side of the feed opening; and suction generating means for generating suction in the capillary tube via said film, said capillary tube comprising:

a first hydrophilic region for transferring the test solution from the test solution feed opening to the reagent;

a second hydrophilic region having a predetermined area maintaining the reagent; and a hydrophobic region which separates the first hydrophilic region from the second hydrophilic region and communicates with the air outlet without passing through the first and second hydrophilic regions.

2. The test device according to claim 1, wherein the film contains the reagent.

3. The test device according to claim 1, wherein the feed opening is blocked with a liquid-permeable, solid-impermeable filter.

4. The test device according to claim 1, wherein the suction generating means is a suction generating chamber the volume of which is changeable.

* * * * *